US009689785B2

(12) United States Patent
Kim et al.

(10) Patent No.: US 9,689,785 B2
(45) Date of Patent: Jun. 27, 2017

(54) METAL OXIDE SEMICONDUCTOR GAS SENSOR HAVING NANOSTRUCTURE AND METHOD FOR MANUFACTURING SAME

(75) Inventors: Jong Kyu Kim, Pohang-si (KR); Hyun Ah Kwon, Busan (KR); Sun Yong Hwang, Gwangyang-si (KR)

(73) Assignee: POSTECH ACADEMY-INDUSTRY FOUNDATION, Pohang-Si, Gyeongsangbuk-Do (KR)

( * ) Notice: Subject to any disclaimer, the term of this patent is extended or adjusted under 35 U.S.C. 154(b) by 225 days.

(21) Appl. No.: 14/407,966

(22) PCT Filed: Jun. 18, 2012

(86) PCT No.: PCT/KR2012/004799
§ 371 (c)(1),
(2), (4) Date: Dec. 15, 2014

(87) PCT Pub. No.: WO2013/191309
PCT Pub. Date: Dec. 27, 2013

(65) Prior Publication Data
US 2015/0137836 A1    May 21, 2015

(51) Int. Cl.
*G01N 5/00* (2006.01)
*G01N 33/00* (2006.01)
*G01N 27/12* (2006.01)

(52) U.S. Cl.
CPC ............... *G01N 5/00* (2013.01); *G01N 27/12* (2013.01); *G01N 27/127* (2013.01); *G01N 33/0009* (2013.01)

(58) Field of Classification Search
CPC .... G01N 5/00; G01N 21/8507; G01N 33/009; G01N 33/0009
See application file for complete search history.

(56) References Cited

U.S. PATENT DOCUMENTS 5,607,564 A * 3/1997 Stormbom ............... C23C 14/14
                                                    204/192.15
6,039,792 A * 3/2000 Calamur ............... B01D 53/228
                                                    55/524

(Continued)

FOREIGN PATENT DOCUMENTS

| JP | 2002-170557 A | 6/2002 |
| JP | 2006-179487 A | 7/2006 |
| KR | 10-2011-0077711 A | 7/2011 |

OTHER PUBLICATIONS

International Search Report for PCT/KR2013/005150 mailed Feb. 28, 2013 from Korean Intellectual Property Office.

*Primary Examiner* — Jeff Natalini
(74) *Attorney, Agent, or Firm* — Revolution IP, PLLC

(57) ABSTRACT

Disclosed is a metal oxide semiconductor gas sensor having a nanostructure, the metal oxide semiconductor gas sensor including: a substrate; a first electrode formed on the substrate; a gas sensing layer provided on the first electrode, made of a metal oxide semiconductor which has a nanostructure and of which electrical conductivity changes when the metal oxide semiconductor reacts with gas to be sensed, and formed by oblique angle deposition; a second electrode formed on the metal oxide semiconductor; and a control unit for measuring the electrical conductivity of the gas sensing layer to sense the gas by applying a predetermined amount of current through the first and the second electrodes.

16 Claims, 11 Drawing Sheets

(56) References Cited

U.S. PATENT DOCUMENTS

| | | | |
|---|---|---|---|
| 2002/0117722 A1* | 8/2002 | Osada | G11C 11/412 257/379 |
| 2006/0091007 A1* | 5/2006 | Inoue | G01N 27/4175 204/406 |
| 2006/0134392 A1 | 6/2006 | Hantschel et al. | |
| 2009/0084677 A1* | 4/2009 | Kawase | G01N 27/4065 204/402 |
| 2009/0183988 A1* | 7/2009 | Imagawa | G01N 27/4062 204/424 |
| 2011/0012086 A1* | 1/2011 | Tsakalakos | G02B 1/118 257/9 |
| 2011/0128489 A1* | 6/2011 | Cho | G02F 1/13439 349/137 |
| 2011/0168261 A1* | 7/2011 | Welser | G02B 1/115 136/259 |

* cited by examiner

[FIG.1]
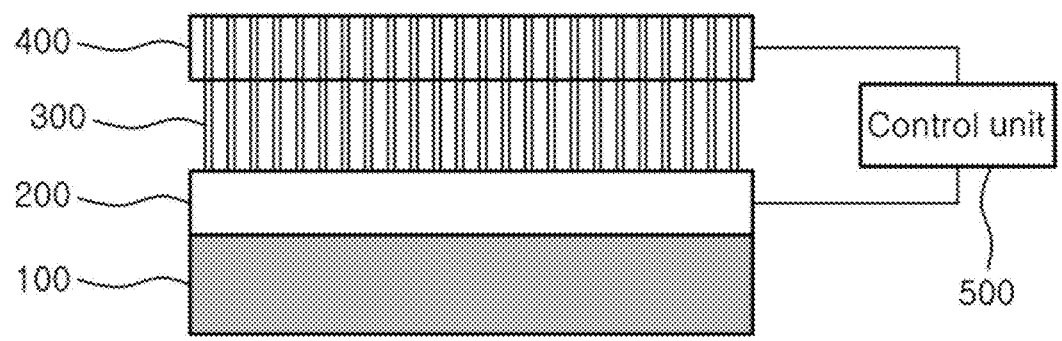
[FIG.2]
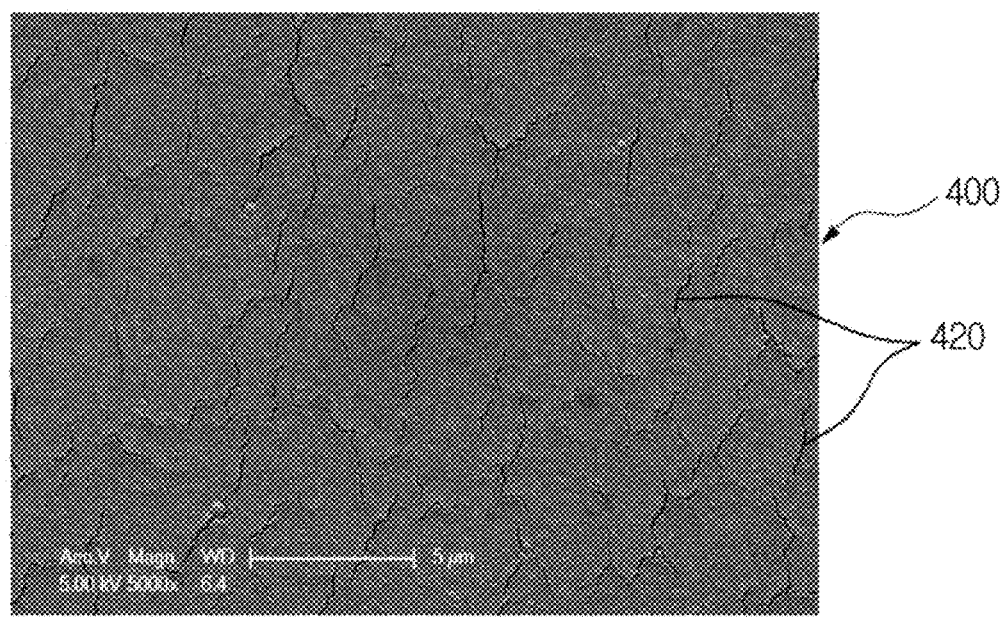

[FIG.3]
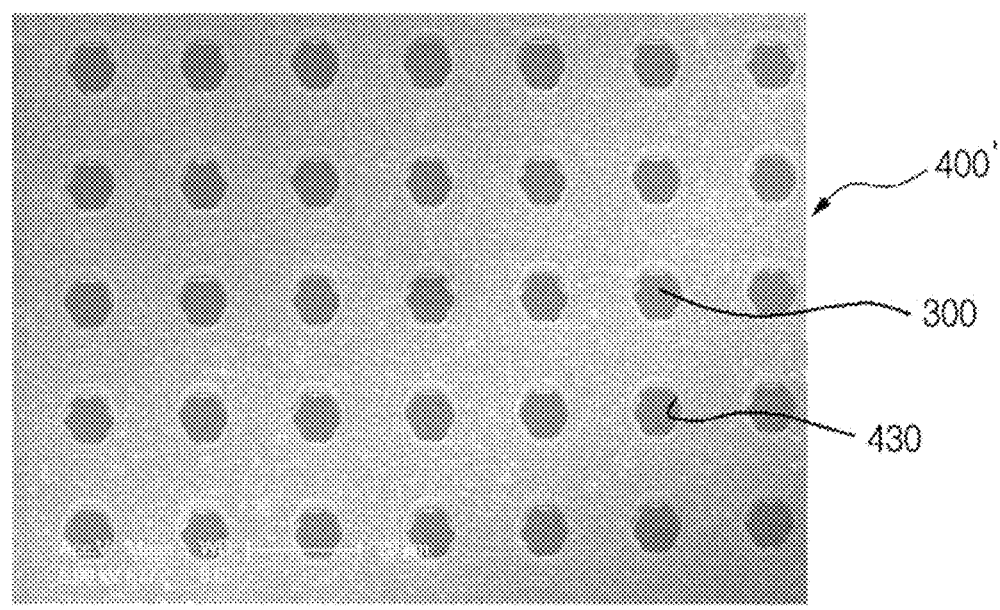

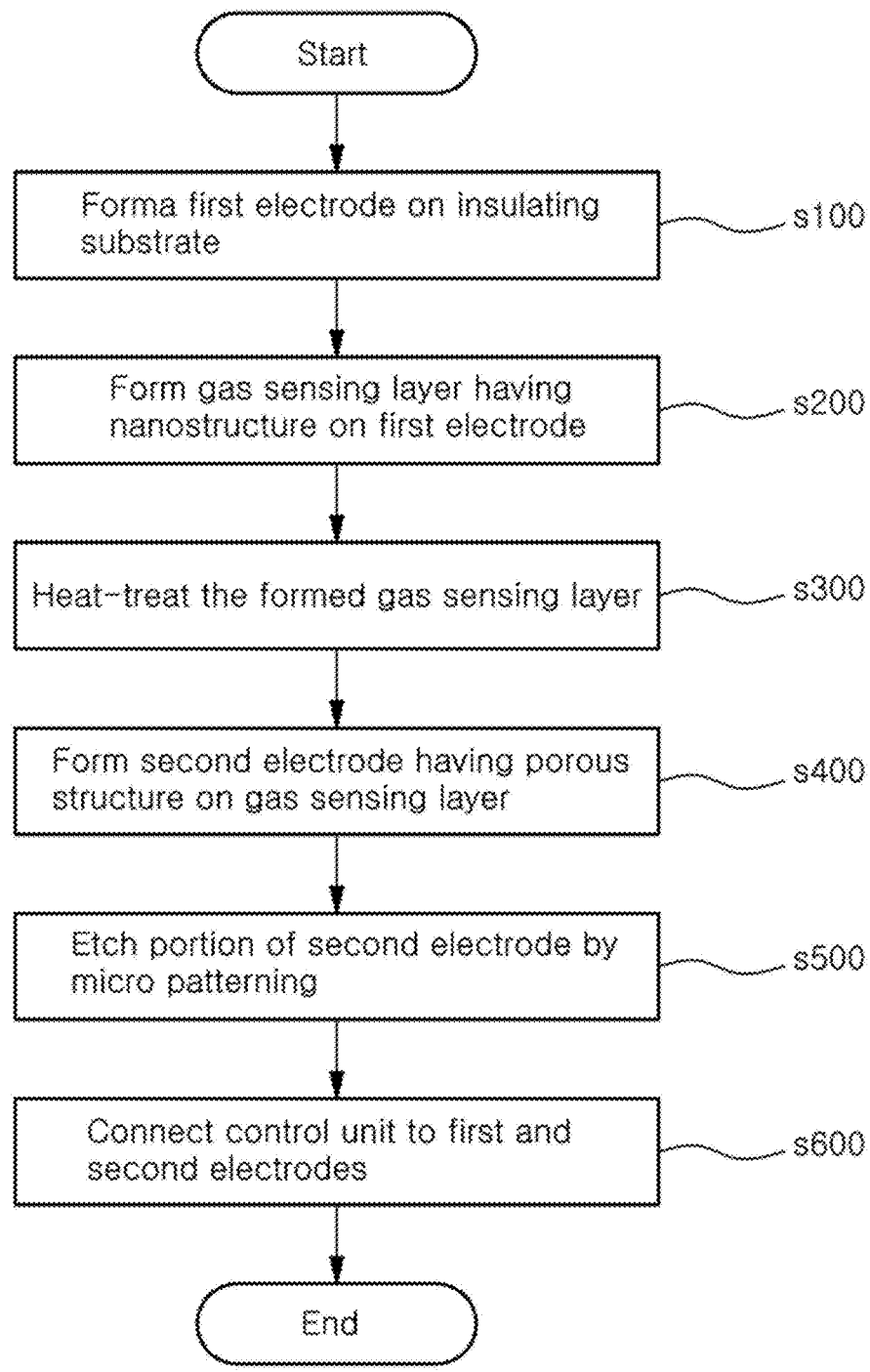

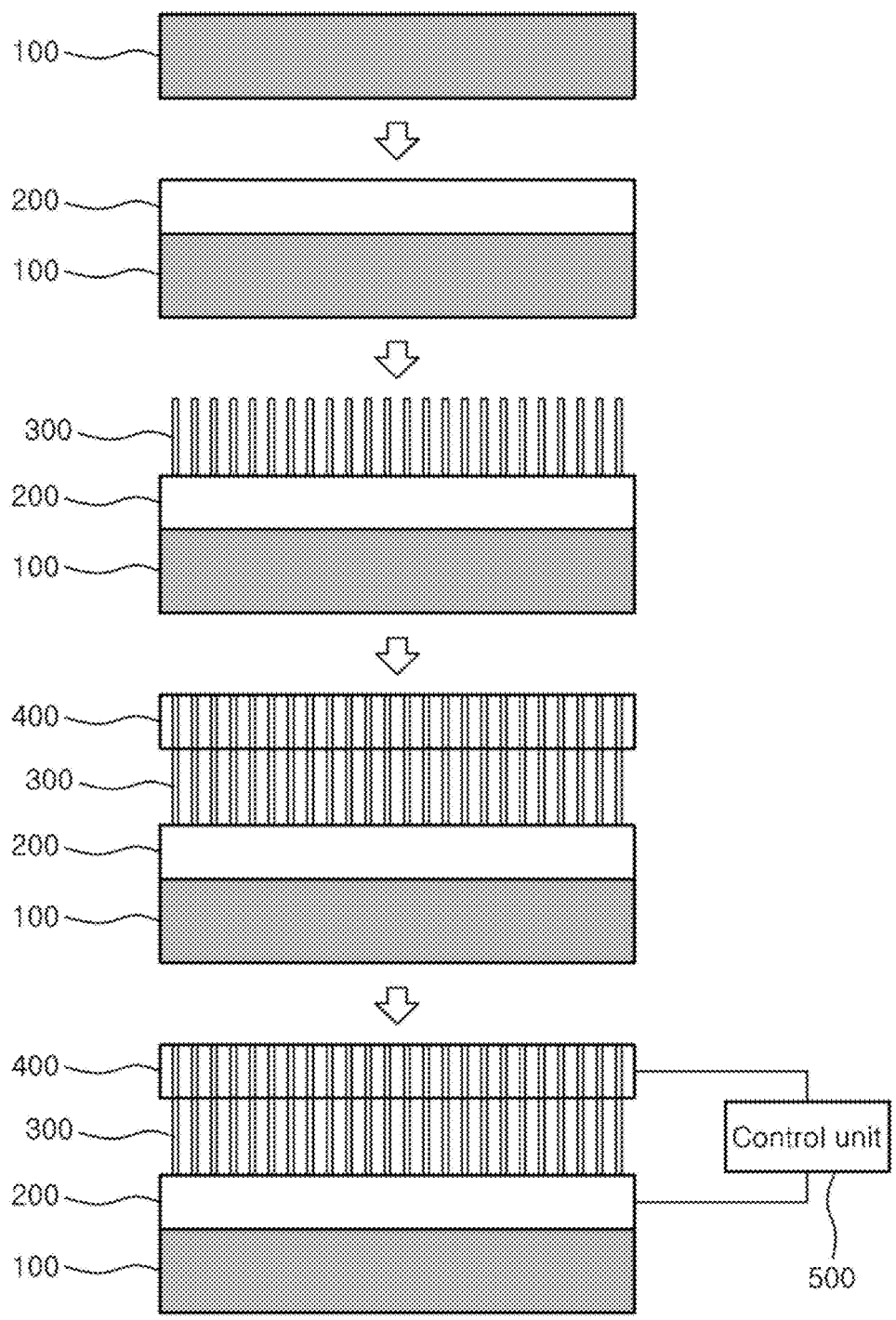

[FIG.6]
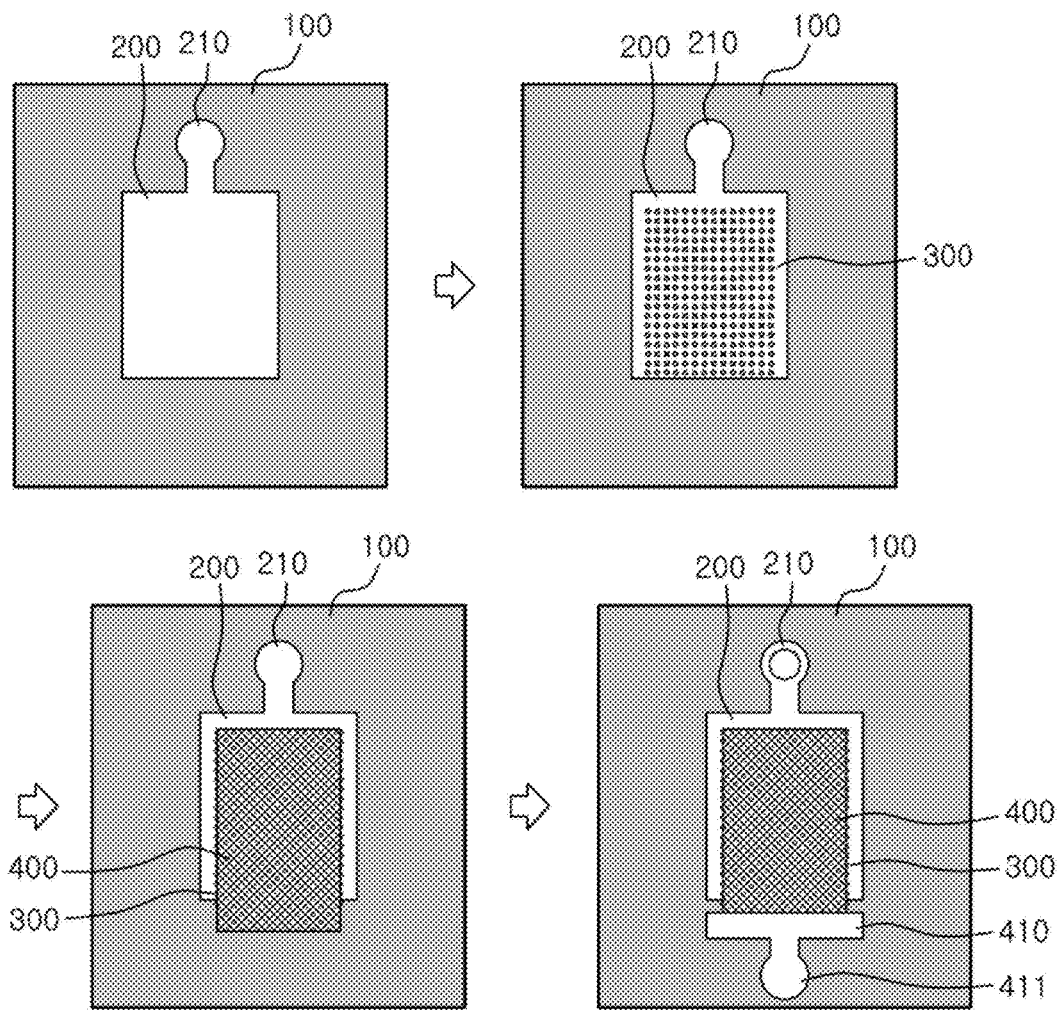

[FIG. 7]
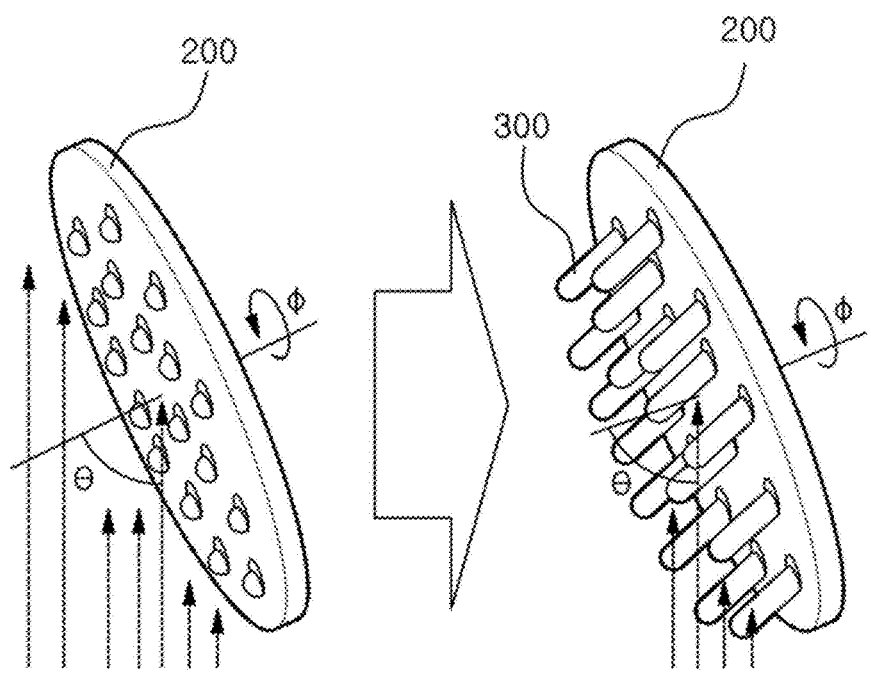
[FIG. 8]
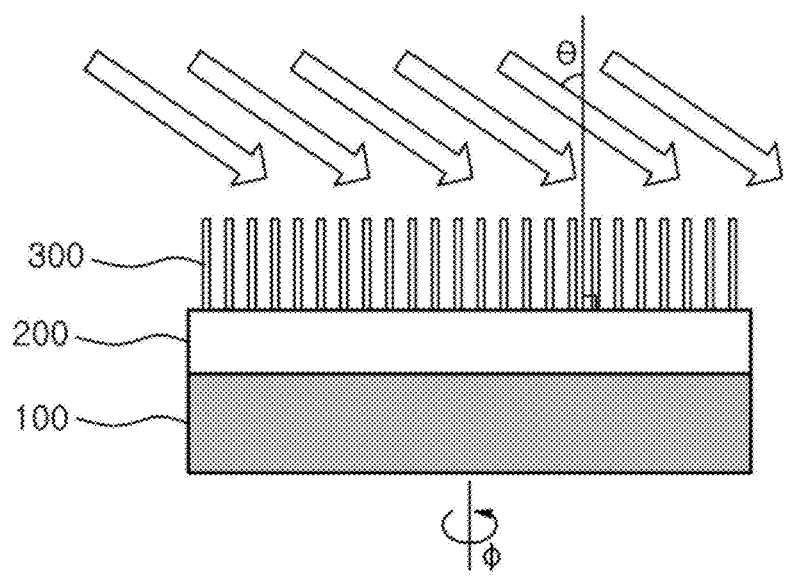

[FIG.9]
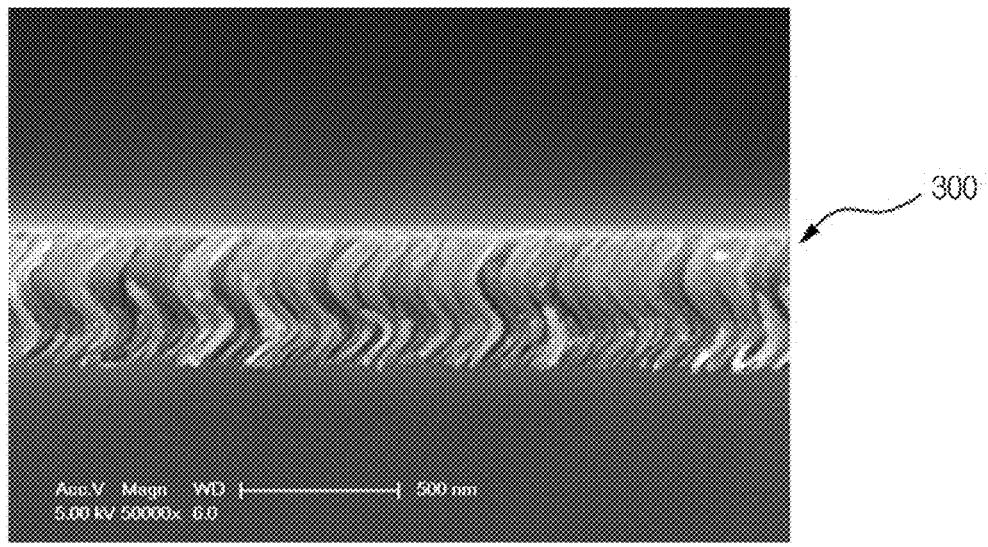
[FIG.10]
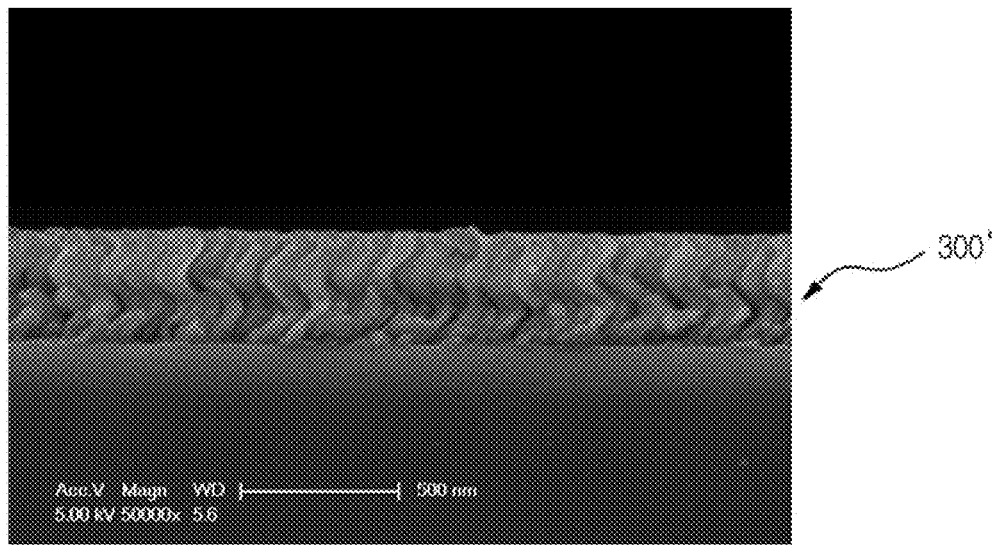

[FIG.11]
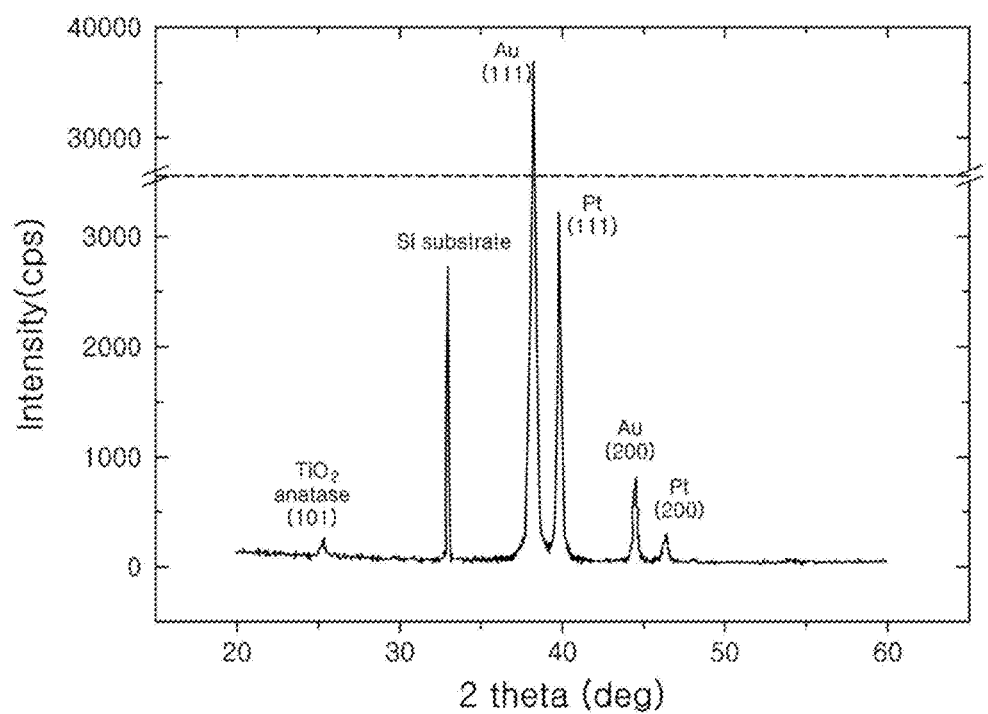

[FIG. 12]
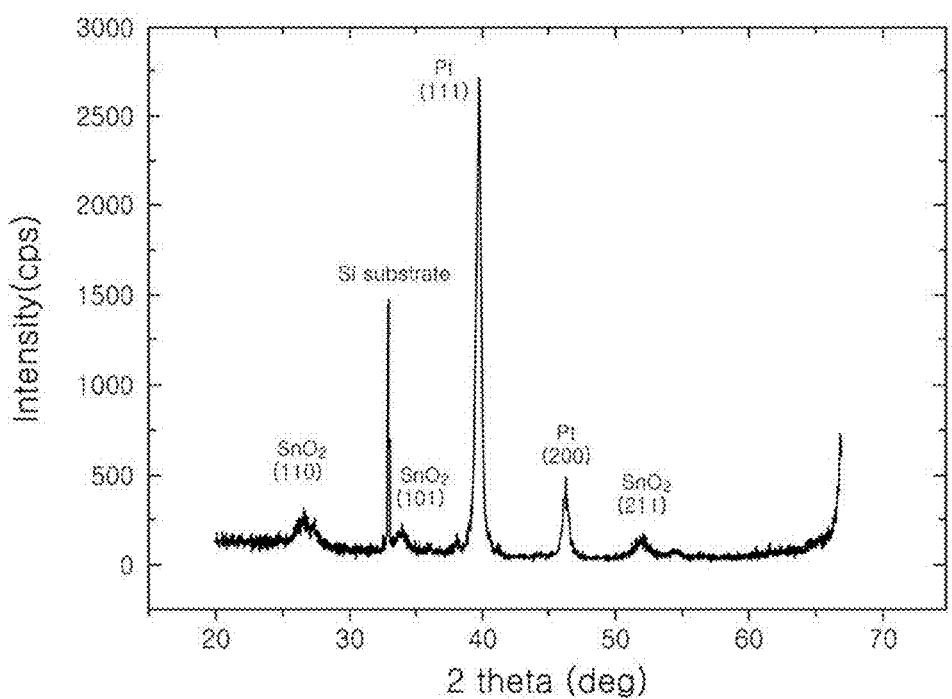
[FIG. 13]
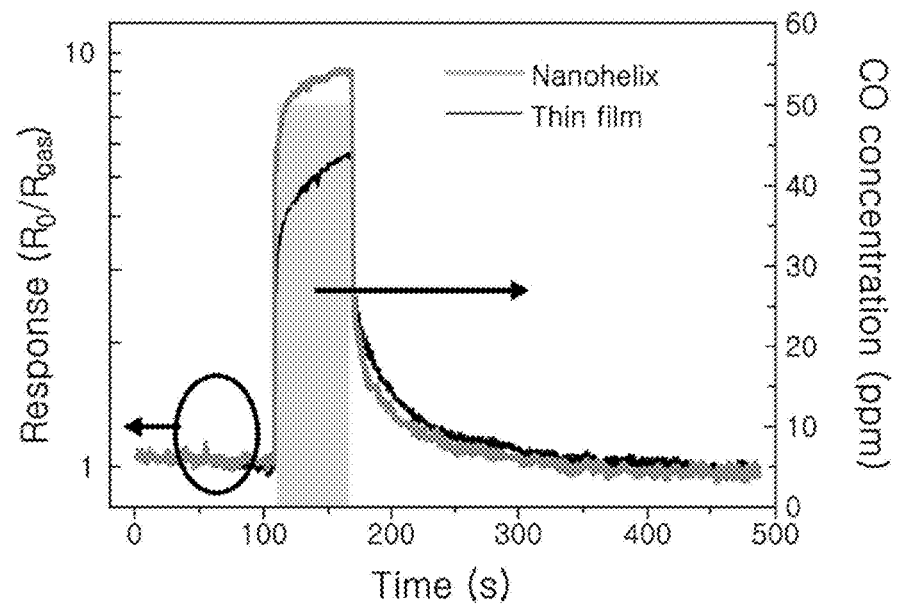

[FIG.14]
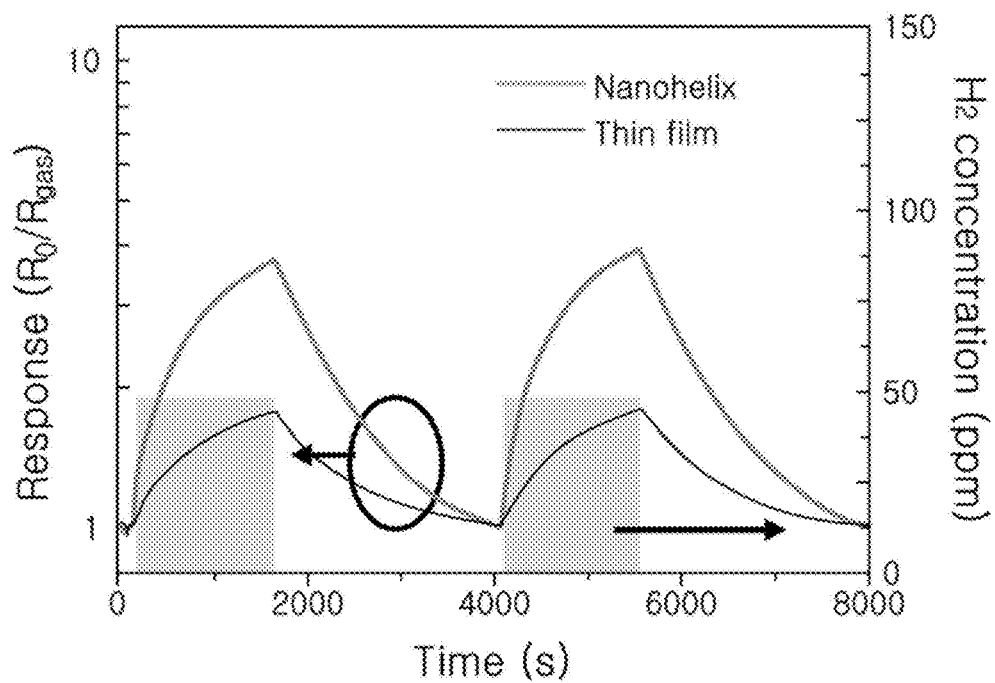

[FIG. 15]
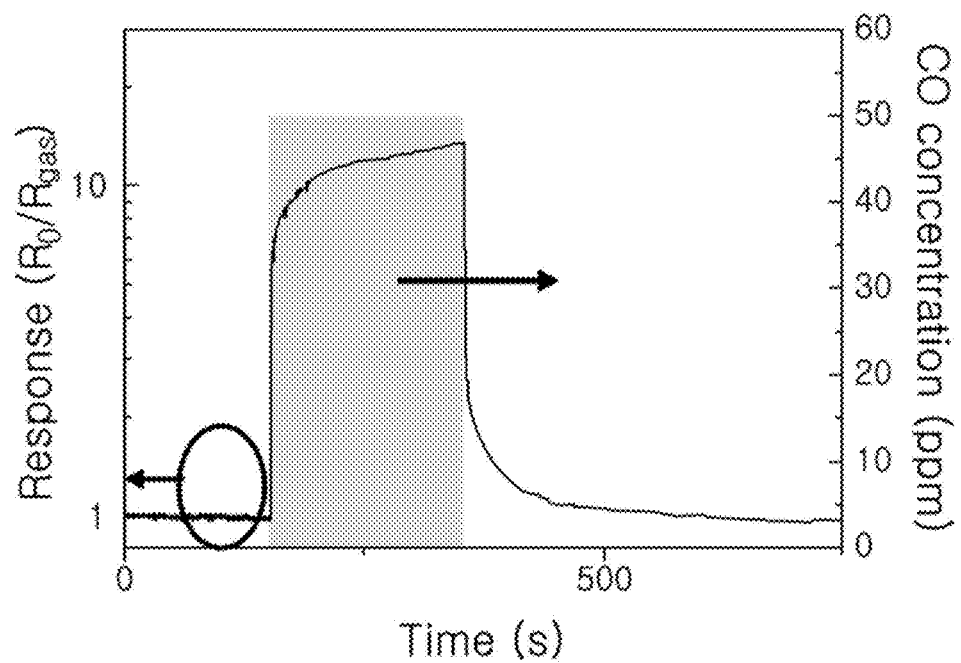

METAL OXIDE SEMICONDUCTOR GAS SENSOR HAVING NANOSTRUCTURE AND METHOD FOR MANUFACTURING SAME

CROSS REFERENCE TO PRIOR APPLICATIONS

This application is a National Stage Application of PCT International Patent Application No. PCT/KR2012/004799 filed on Jun. 18, 2012, under 35 U.S.C. §371, which is hereby incorporated by reference in its entirety.

TECHNICAL FIELD

The present invention relates to a metal oxide semiconductor gas sensor having a nanostructure and a method for manufacturing the same, and more particularly, to a metal oxide semiconductor gas sensor having a nanostructure and a method for manufacturing the same, in which the metal oxide semiconductor formed into a nanostructure by oblique angle deposition may be used as a gas sensing layer of a gas sensor, and may also keep its existing advantages such as maximization of reactivity with gas.

BACKGROUND ART

In general, a metal oxide semiconductor gas sensor is a sensor for sensing a gas from an object in a way of measuring a change in electrical conductivity occurring when a metal oxide semiconductor reacts with the gas.

Such a metal oxide semiconductor gas sensor can be inexpensively manufactured in a small size, and also has a number of advantages, such as a high stability at high temperature as well as high sensitivity and fast response speed, so that the metal oxide semiconductor gas sensor is widely used.

In particular, in the case of using a metal oxide semiconductor having a nanostructure, it is possible to maximize a reaction between the metal oxide semiconductor and the gas, due to nanostructure's inherent characteristics of a large specific surface area, due to characteristics of an electron path being several tens of nm or less when compared to a depletion layer of a sensor surface being several tens of nm or less, and due to characteristics of a gas being able to be rapidly diffused into the metal oxide semiconductor having a nanostructure having a large porosity, and thus to further enhance the above-described advantages of the metal oxide semiconductor gas sensor.

However, a gas sensing layer including the metal oxide semiconductor needs to be interposed between a pair of electrodes because the metal oxide semiconductor should sense electrical conductivity. This however brings about problems in that effective contact between the gas and the gas sensing layer is interrupted, resulting in degradation of characteristics such as sensitivity and response speed.

Meanwhile, a method of growing a nano-wire using chemical vapor deposition, a method of preparing a sensing layer using a colloidal template, a method of forming a nano-fiber layer using an electro-spinning, a method of forming a surface nanostructure using a laser, a surface etching method using anodized aluminum oxide or the like, has been used as a conventional method for forming such a nanostructure.

However, such methods for forming a nanostructure have major downsides in terms of production costs, simplicity of the method, integrability and arrayablity.

First, when a nanostructure is formed by chemical vapor deposition, reproducibility is significantly reduced. Especially, in the case of a nano-wire, it is difficult to constantly control a thickness, length, growth direction, etc., of the nano-wire in each process, thus making it difficult to manufacture a device having the same performance even through the same process. Furthermore, the chemical vapor deposition for forming a nanostructure includes a high-temperature process and a chemical reaction, thus making it difficult to integrate and array the sensor.

Also, a method of forming a nanostructure by forming a nano-pattern and etching a surface by using a colloidal template, anodized aluminum oxide, an electron beam lithography, a nano-imprint, a nano-sphere, etc., provides disadvantages such as complicated process steps and high production costs.

In addition, the method is difficult to achieve a large-sized device and is not a process of manufacturing a general semiconductor micro device. Thus, there may be a problem in compatibility with other device fabrication processes, such as an electronic nose fabrication.

Furthermore, a method for forming a nanostructure on a surface by using a laser has a relatively simple process step, but a specific surface area the nanostructure is not greater than those obtained by other methods. Moreover, it may be difficult to control a shape of the nanostructure, and it may be problematic in bond formation by an exposure to laser radiation and compatibility with other device fabrication.

To overcome these disadvantages, there is a method of forming a nanostructure by using oblique angle deposition. The oblique angle deposition, which is a method of performing deposition while a substrate makes a certain oblique angle with a flux direction of a deposition material, enables a high-porosity thin film having a nanostructure to be formed, due to a selfshadowing effect caused by a surface diffusion of a deposition material and an initial deposition material.

In addition, the oblique angle deposition may use physical vapor depositions, such as electron beam evaporation, sputter deposition, and pulsed laser deposition, which are widely used in a semiconductor micro device fabrication, and is thus very suitable for miniaturization, integration, simplification in arraying, and enlargement of the gas sensor device.

A humidity sensor with a nanostructure manufactured by the oblique angle deposition has been previously reported. Since the humidity sensor uses a change in an optical property of an oxide thin film, it is possible to fully make use of an advantage of a nanostructure formed by the oblique angle deposition with only a substrate disposed under the thin film.

A gas sensor for sensing a reducing or oxidizing gas should measure a change in electrical conductivity of a metal oxide thin film but cannot measure the change in electrical conductivity with an existing configuration on the substrate. Therefore, upper and lower electrodes need to be provided with a metal oxide thin film interposed therebetween. However, in this case, a gas and a metal oxide thin film as a gas sensing layer are not efficiently brought into contact with each other, thus making it difficult to realize performance of the gas sensor.

To explain in more detail, since a metal oxide thin film formed using the oblique angle deposition has a nanostructure array vertically arranged, electrical conductivity in a direction parallel to a substrate is difficult to be obtained, so that a change in conductivity between lower electrodes is difficult to be measured without an upper electrode.

Furthermore, when the gas sensor is configured with only the lower electrodes without the upper electrode, it has a nanostructure having a moving path of an electron between the lower electrodes. In this case, a contact area between the substrate and the nanostructures increases, and it is thus undesirable to measure a minute change in electrical conductivity.

Accordingly, the upper electrode is necessary. Here, the upper electrode should connect every upper portion of the nanostructure array, and should prevent a short with the lower electrode caused by deposition of an electrode material on a side surface of the nanostructure. This is because an electron path does not form through the metal oxide semiconductor, but through the electrode material.

In order to form the upper electrode, complex processes should be performed such as formation of a nanostructure, coating of a resist, exposure of the nanostructure by etching, deposition of an electrode, additional removal of the resist or the like. This is not an easy way in terms of cost and process simplification, and also not a desirable method in terms of compatibility with a semiconductor micro device manufacturing process since coating and etching, etc., should be performed.

Because of such difficulties, there has been no case of applying a metal oxide having a nanostructure manufactured by using an oblique angle deposition having the above-mentioned advantages, to a gas sensor of sensing a reducing gas and an oxidizing gas.

DISCLOSURE OF THE INVENTION

Technical Problem

To solve the above described problems, the present invention provides a metal oxide semiconductor having a nanostructure and a method for manufacturing the same, in which the metal oxide semiconductor easily formed into a nanostructure by oblique angle deposition may be used as a gas sensing layer of a gas sensor interposed between a pair of electrodes, and for this, an electrode on the gas sensing layer may be easily manufactured, and the gas sensing layer and a gas to be sensed may be guaranteed to be brought freely into a contact each other, and also the metal oxide semiconductor having the nanostructure may keep its existing advantages such as maximization of reactivity with gas.

Technical Solution

To solve the above described problems, a metal oxide semiconductor having a nanostructure, according to the present invention, includes: a substrate; a first electrode formed on the substrate; a gas sensing layer provided on the first electrode, made of a metal oxide semiconductor which has a nanostructure and of which electrical conductivity changes when the metal oxide semiconductor reacts with gas to be sensed, and formed by oblique angle deposition; a second electrode formed on the metal oxide semiconductor; and a control unit for measuring the electrical conductivity of the gas sensing layer to sense the gas by applying a predetermined amount of current through the first and the second electrodes.

The second electrode may be formed to have a porous structure.

The second electrode may be provided to have a plurality of crevices in mesh shape.

The metal oxide semiconductor may have the nanostructure of any one shape of a nano-helix, a nano-rod, an inclined nano-rod, a nano-wire, a nano-ribbon, a nano-spring and a nano-cone.

The metal oxide semiconductor may be made of at least one of $SnO_2$, $TiO_2$, ZnO, CuO, NiO, CoO, $In_2O_3$, $WO_3$, MgO, CaO, $La_2O_3$, $Nd_2O_3$, $Y_2O_3$, $CeO_2$, PbO, $ZrO_2$, $Fe_2O_3$, $Bi_2O_3$, $V_2O_5$, $VO_2$, $Nb_2O_5$, $Co_3O_4$ and $Al_2O_3$.

Each of the first and second electrodes may be made of at least one of Pt, Au, Ti, Pd, Ir, Ag, Ru, Ni, STS, Al, Mo, Cr, Cu, W, ITO (Sn doped $In_2O_3$) and FTO (F doped $SnO_2$).

The substrate may be provided in an insulating substrate made of an insulation material, or a conductive substrate insulated with an insulation material.

The substrate may be provided in any one of an alumina substrate, a sapphire substrate and a silicon substrate, a metal substrate, a conductive oxide substrate and a conductive polymer substrate on which an insulation layer made of an insulation material is deposited.

The second electrode may include one or more through holes formed by micro-patterning.

The second electrode may be provided with an electrode pad for measuring an electrical property through a probe and for wire-bonding to an external circuit.

According to a preferred embodiment of the present invention, a method for manufacturing a metal oxide semiconductor gas sensor having a nanostructure, the method includes: forming a first electrode on a substrate; forming a gas sensing layer by depositing a deposition material at a predetermined oblique angle with respect to an upper surface of the first electrode through oblique angle deposition to allow a metal oxide having a nanostructure to be formed on the upper surface of the first electrode; forming a second electrode on the gas sensing layer; and connecting a control unit measuring electrical conductivity of the gas sensing layer to the first and second electrodes.

The forming of the second electrode may include forming the second electrode having a porous structure on the gas sensing layer by using the oblique angle deposition.

The forming of the second electrode may include forming the second electrode having a plurality of crevices in a mesh shape on the gas sensing layer by using oblique angle deposition.

The forming of the gas sensing layer may be forming the gas sensing layer by depositing the metal oxide while rotating the first electrode at a predetermined speed in a predetermined direction in a state where a flux line of the metal oxide as a deposition material makes a predetermined oblique angle with an upper surface of the first electrode.

The forming of the gas sensing layer may be forming the gas sensing layer by depositing the metal oxide in a state where a flux line of the metal oxide as a deposition material makes an angle in the range of 30 to 90 degrees (exclusive of 90) with a vertical line to the upper surface of the first electrode.

The method for manufacturing a metal oxide semiconductor gas sensor having a nanostructure further includes forming a plurality of through holes by micro-pattering the second electrode to allowing the gas to easily flow into and out of the gas sensing layer.

The method for manufacturing a metal oxide semiconductor gas sensor having a nanostructure may further include heat-treating the gas sensing layer at 300° C. to 1,000° C. so that the gas sensing layer is crystallized.

The method for manufacturing a metal oxide semiconductor gas sensor having a nanostructure may further include performing heat treatment at 200° C. to 1,000° C. so that the gas sensing layer makes ohmic contact to the first and second electrodes.

Advantageous Effects

According to a metal oxide semiconductor gas sensor having a nanostructure and a method for manufacturing the same of the present invention, the metal oxide semiconductor gas sensor having a nanostructure formed by oblique angle deposition having a number of advantages, such as integration, simplification in production process, enlargement and high reproducibility, is applicable to a gas sensing layer interposed between the first and second electrodes.

Also, since the second electrode is formed in the porous structure, the second electrode easily brings the gas sensing layer into contact with a gas to be sensed, thus further improving sensitivity of the gas sensor.

Since the gas to be sensed may easily flow in and out through the second electrode having the porous structure, the metal oxide semiconductor having the nanostructure is effectively used as the gas sensing layer interposed between one pair of electrodes and also may keep its existing advantages such as maximization of reactivity with a gas.

In other words, since the gas sensing layer of the gas sensor may be manufactured by using electron beam evaporation or sputter deposition or pulsed laser deposition, as a specific method and also a physical vapor deposition method for oblique angle deposition, reproducibility of the process is excellent.

Further, in the case of forming the gas sensing layer having the nanostructure by using such physical vapor deposition, since using an oblique angle is the only difference from the conventional processes, compatibility with existing semiconductor processes is good. Accordingly, miniaturization, integration and arrayablity of the gas sensor and integration of the process are easy.

In particular, since the oblique angle deposition is applicable to a process such as lithography, the gas sensing layer having a nanostructure may be exactly manufactured with a desired pattern in a desired size at a desired position. That is, the oblique angle deposition is excellent in compatibility with a micro-production process. Accordingly, a manufacturing process of electronic nose may be simplified.

When the metal oxide semiconductor having a nanostructure is formed by using such oblique angle deposition, the shape of the nanostructure may be freely changed into various shapes to maximize the reaction with the gas by adjusting a rotation speed of the first electrode, pattern of direction and oblique angle.

Further, by disposing the first and second electrodes on and under the metal oxide semiconductor having a nanostructure, a depletion layer of the metal oxide semiconductor having a nanostructure may be used effectively to change electrical conductivity, thus maximizing the gas sensitivity.

In addition, by forming the second electrode on the gas sensing layer made of the metal oxide semiconductor having a nanostructure by the oblique angle deposition, an upper section of the gas sensing layer is electrically connected without an additional process, a space required for inflow and outflow of the gas is also secured, and unwanted short-circuit of the first and second electrodes is prevented from occurring.

Also, the gas to be sensed may be brought into a contact with the gas sensing layer more easily by etching a portion of the second electrode through micro-patterning.

In addition, durability of the gas sensing layer itself may be improved by heat treating and crystallizing the gas sensing layer at 300° C. or higher, and the first and second electrodes are rigidly brought into an ohmic contact with the gas sensing layer by performing heat treatment at 200° C. or higher after the gas sensing layer provided on the first electrode and the second electrode are formed, thus further improving the durability.

BRIEF DESCRIPTION OF THE DRAWINGS

FIG. 1 is a schematic diagram of a metal oxide semiconductor gas sensor having a nanostructure according to a preferred embodiment of the present invention.

FIG. 2 is a plane scanning electron micrograph of a second electrode provided in a metal oxide semiconductor gas sensor having a nanostructure, according to a preferred embodiment of the present invention.

FIG. 3 is a plane scanning electron micrograph of a second electrode provided in a metal oxide semiconductor gas sensor having a nanostructure according to another embodiment of the present invention.

FIG. 4 is a flowchart of a method for manufacturing a metal oxide semiconductor gas sensor having a nanostructure according to a preferred embodiment of the present invention.

FIG. 5 is a schematic side view illustrating a method for manufacturing a metal oxide semiconductor gas sensor having a nanostructure in sequence according to a preferred embodiment of the present invention.

FIG. 6 is a schematic plan view illustrating a method for manufacturing a metal oxide semiconductor gas sensor having a nanostructure in sequence according to a preferred embodiment of the present invention.

FIG. 7 is a perspective view illustrating oblique angle deposition by which a gas sensing layer having a nanostructure is formed, in a method for manufacturing a metal oxide semiconductor gas sensor having a nanostructure according to a preferred embodiment of the present invention.

FIG. 8 is a schematic side view illustrating oblique angle deposition by which a gas sensing layer having a nanostructure is formed, in a method of manufacturing a metal oxide semiconductor gas sensor having a nanostructure according to a preferred embodiment of the present invention.

FIG. 9 is a cross-sectional scanning electron micrograph of a $TiO_2$ gas sensing layer formed by a method for manufacturing a metal oxide semiconductor gas sensor having a nanostructure according to a preferred embodiment of the present invention.

FIG. 10 is a cross-sectional scanning electron micrograph of a $SnO_2$ gas sensing layer formed by a method for manufacturing a metal oxide semiconductor gas sensor having a nanostructure according to a preferred embodiment of the present invention.

FIG. 11 is an X-ray diffraction graph showing crystallization of a $TiO_2$ gas sensing layer formed by a heat treatment in a method for manufacturing a metal oxide semiconductor gas sensor having a nanostructure according to a preferred embodiment of the present invention.

FIG. 12 is an X-ray diffraction graph showing crystallization of a $SnO_2$ gas sensing layer formed by a heat treatment in a method for manufacturing a metal oxide semiconductor gas sensor having a nanostructure according to a preferred embodiment of the present invention.

FIGS. 13 and 14 are graphs respectively showing sensitivity of a $TiO_2$ gas sensing layer versus a concentration of CO gas and a concentration of $H_2$ gas at 250° (wherein a sample in which a $TiO_2$ thin film is deposited on an IDE (interdigitated electrode) structure is used as a comparison sample), in a metal oxide semiconductor gas sensor manufactured by a method for manufacturing a metal oxide semiconductor gas sensor having a nanostructure according to a preferred embodiment of the present invention.

FIG. 15 is a graph showing sensitivity of a $SnO_2$ gas sensing layer versus a concentration of CO gas at 250°, in a metal oxide semiconductor gas sensor manufactured by a method for manufacturing a metal oxide semiconductor gas sensor having a nanostructure according to a preferred embodiment of the present invention.

BEST MODE FOR CARRYING OUT THE INVENTION

Hereinafter, embodiments of the present invention will be described in detail with reference to the accompanying drawings to fully explain the present invention in such a manner that it may easily be carried out by a person with ordinary skill in the art (hereinafter, abbreviated 'those skilled in the art') to which the present invention pertains. The invention may, however, be embodied in many different forms and should not be construed as being limited to the embodiments set forth herein.

Hereinafter, operations and effects of a metal oxide semiconductor gas sensor having a nanostructure according to a preferred embodiment of the present invention will be described in detail with reference to the accompanying FIGS. 1 to 3 and FIG. 6.

A metal oxide semiconductor gas sensor having a nanostructure according to a preferred embodiment of the present invention includes a substrate 100, a first electrode 200, a gas sensing layer 300, a second electrode 400, and a control unit 500.

While the substrate 100 may be provided in an insulating substrate or a conductive substrate, and more specifically, a sapphire substrate, a silicon oxide substrate, an alumina substrate, or a metal substrate on which an insulating layer made of an insulating material is deposited, a conductive oxide substrate, a silicon substrate or the like, the first electrode 200 and the second electrode 400 should be insulated from each other so as not to cause a short-circuit.

In particular, when a conductive substrate is used as the substrate 100, a highly conductive semiconductor such as doped silicon, a metal such as stainless steel, a conductive oxide, a conductive polymer may be used as a material for the substrate. In this case, an additional insulation using an insulation material is required between the first and second electrodes 200 and 400.

The first electrode 200 is formed on the substrate 100 by patterning using lithography, and may be formed of one or more selected from Pt, Au, Ti, Pd, Ir, Ag, Ru, Ni, STS, Al, Mo, Cr, Cu, W, ITO (Sn doped $In_2O_3$) and FTO (F doped $SnO_2$).

The first electrode 200 may be provided with a first electrode pad 210 connected to a connecting line connected to the control unit 500.

The gas sensing layer 300 is made of a metal oxide semiconductor having a nanostructure formed by oblique angle deposition, and is formed on the first electrode 200. In more detail, a portion of a metal oxide semiconductor layer is patterned into a nanostructure on the first electrode 200 by the lithography.

The metal oxide semiconductor having a nanostructure and constituting the gas sensing layer 300 is formed by using the oblique angle deposition, and more specifically, may be formed by depositing a metal oxide while rotating the first electrode 200 at a predetermined speed in a predetermined direction of a pattern in a state where a flux line of the metal oxide as a deposition material makes a predetermined oblique angle with the upper surface of the first electrode 200.

Here, the nanostructure of the metal oxide semiconductor may be realized as a nanostructure of any one of a nano-helix, a nano-rod, an inclined nano-rod, a nano-wire, a nano-ribbon, a nano-spring and a nano-cone formed according to the above-mentioned changes in the rotation speed, the direction and the oblique angle of the first electrode 200.

At this point, it is preferable that the flux line of the metal oxide as a deposition material make an angle in the range of 30 to 90 degrees (exclusive of 90) as an inclination angle with a vertical line to the upper surface of the first electrode 200.

Here, the metal oxide semiconductor may be at least one of $SnO_2$, $TiO_2$, ZnO, CuO, NiO, CoO, $In_2O_3$, $WO_3$, MgO, CaO, $La_2O_3$, $Nd_2O_3$, $Y_2O_3$, $CeO_2$, PbO, $ZrO_2$, $Fe_2O_3$, $Bi_2O_3$, $V_2O_5$, $VO_2$, $Nb_2O_5$, $Co_3O_4$ and $Al_2O_3$.

The second electrode 400 is formed in a porous structure on the gas sensing layer 300 by lithography. In particular, the second electrode 400 may be formed by the oblique angle deposition. At this time, the second electrode 400 may be formed to have a plurality of crevices 420 in a mesh shape by varying an oblique angle of deposition and deposition thickness when the second electrode 400 is deposited.

FIG. 2 is a plane scanning electron micrograph of the second electrode 400 having a porous structure having the plurality of crevices 420 in a mesh shape formed by the above mentioned oblique angle deposition.

Thus, since the second electrode 400 has a porous structure having the plurality of crevices 420 in the mesh shape, the gas to be sensed may freely flow in and out of the gas sensing layer 300 to react with the metal oxide semiconductor having the nanostructure.

The meaning of 'porous structure' used in the description of preferred embodiments of the present invention does not indicate a structure in which a number of holes are formed in a narrow sense, but indicate a permeable structure in which a fluid is allowed to pass through in a broad sense.

Similarly to the first electrode 200, the second electrode 400 may selectively use one or more of Pt, Au, Ti, Pd, Ir, Ag, Ru, Ni, STS, Al, Mo, Cr, Cu, W, ITO (Sn doped $In_2O_3$) and FTO (F doped $SnO_2$).

Also, it is preferable that an electrode pad 410 provided with a second electrode pad 411 is additionally formed on the second electrode 400 so as to measure an electrical property through a probe and to perform wire bonding to an external circuit. The pad electrode 410 is formed on the second electrode 400 through patterning of a metal electrode.

In a preferred embodiment of the present invention, while the second electrode 400 is realized to have a mesh shape with a plurality of holes 420 by using the oblique angle deposition, the porous structure may not be provided. This is because inflow and outflow of the gas to be sensed through a side section of the gas sensing layer 300 are possible even if the second electrode 400 does not have a porous structure.

On the other hand, as another embodiment of the present invention, as shown in FIG. 3, a plurality of through holes 430 may be formed on a second electrode 400' by micro patterning so that the gas to be sensed is allowed to more freely flow in and out of the gas sensing layer 300. When the gas to be sensed flows in through the plurality of through holes 430, the gas may easily contact the gas sensing layer 300, so that reaction may take place more easily.

The control unit 500 is connected to the first and second electrodes 200 and 400 through a connection line and allows a predetermined amount of current to flow through the first and second electrodes 200 and 400 to measure the electrical conductivity of the gas sensing layer 300, thus sensing the gas to be sensed.

MODE FOR CARRYING OUT THE INVENTION

Hereinafter, a method for manufacturing a metal oxide semiconductor gas sensor having a nanostructure according to a preferred embodiment of the present invention will be described in detail with reference to the accompanying FIGS. 4 to 15.

First, a first electrode 200 is formed on a substrate 100 made of sapphire by patterning a layer of Pt as an electrode material as shown in FIGS. 5 and 6 (s100). At this time, when a conductive substrate is used as the substrate 100, an insulating process may be further performed for first and second electrodes 200 and 400 which are formed later.

Next, as shown in FIG. 7, a gas sensing layer 300 having a nanostructure is formed on the first electrode 200 by oblique angle deposition (s200).

In more detail, metal oxides, $TiO_2$ and $SnO_2$ are deposited on the first electrode 200 by electron beam deposition. At this time, the deposition is conducted in a state where a flux line of the metal oxide as a deposition material makes an angle ($\theta$) of 80 degrees with a vertical line to an upper surface of the first electrode 200, and the first electrode 200 rotates (in $\phi$-direction) about the center thereof to additionally form a nano-helix shape among three-dimensional nano shapes. The rotational rate is maintained at 0.1 rpm and the deposition is conducted at a deposition rate of 2.5 A/s.

A cross-sectional scanning electron micrograph (×50,000 magnification) of the $TiO_2$ gas sensing layer 300 manufactured through the above-described process is shown in FIG. 9. A cross-sectional scanning electron micrograph (×50,000 magnification) of the $SnO_2$ gas sensing layer 300' manufactured through the same process is shown in FIG. 10.

Here, the three-dimensional nano-shape of the metal oxide semiconductor constituting the gas sensing layer 300 is not limited to the nano-helix shape, and may be realized in the shape of, for example, a nano-rod, an inclined nano-rod, a nano-wire, a nano-ribbon, a nano-spring, a nano-cone or the like.

Next, heat treatment is performed for 30 minutes at 500° C. degrees to activate the $TiO_2$ gas sensing layer 300 formed on the first electrode 200 (s300). The gas sensing layer 300 is crystallized through the heat treatment and an anatase diffraction peak (101) is observed by an x-ray diffraction test of FIG. 11.

Furthermore, a $SnO_2$ gas sensing layer 300' is heat-treated for 3 hours at 550° C. An x-ray diffraction test result is shown in FIG. 12, and diffraction peaks of (110), (101), and (211) are observed.

From such an x-ray diffraction test result, it can be confirmed that the $TiO_2$ gas sensing layer 300 and the $SnO_2$ gas sensing layer 300' are crystallized.

Here, the temperature of the heat treatment for crystallization of the gas sensing layers 300 and 300' is not limited to 500° C. or 550° C., and may be determined in the range of 300° C. to 1,000° C.

Thereafter, the second electrode 400 having a porous structure is formed on the gas sensing layer 300 through patterning as shown in FIG. 6 (s400). The second electrode 400 uses the oblique angle deposition as shown in FIG. 8, and at this point, the second electrode 400 of Au is deposited while a flux line of Au as a deposition material makes an angle ($\theta'$) of 45 degrees with a vertical line to the upper surface of the gas sensing layer 300 or the first electrode 200.

At this time, the second electrode 400 is continuously deposited on the gas sensing layer 300 having a nanostructure to have a porous structure through which the gas may easily pass.

Thus, the second electrode 400 may have a plurality of crevices 420 formed in a mesh shape by varying oblique angle of deposition and deposition thickness when the second electrode 400 is formed by deposition.

Next, one or more through holes are formed by micro-patterning (etching) a portion of the second electrode 400 such that the gas to be sensed more easily flow in and out of the second electrode 400 (s500), and the control unit 500 is connected to the first and second electrodes 200 and 400 and installed (s600).

In a preferred embodiment of the present invention, a photolithography is used as patterning for excellent compatibility with a micro fabrication process.

Next, a heat treatment process at 200° C. to 1,000° C. may be additionally conducted so that the gas sensing layer 300 makes ohmic contact to the first and second electrodes 200 and 400.

Further, for an effective ohmic contact between the gas sensing layer 300 and the second electrode 400, a Ti bonding layer may be additionally deposited prior to the formation of the second electrode 400 by deposition.

Meanwhile, in a preferred embodiment of the present invention, although the second electrode 400 is formed in a porous structure, such as a structure having a plurality of crevices 420 formed in a mesh shape by the oblique angle deposition, and one or more through holes are formed by micro-pattering a portion of the second electrode 400, the forming process of the porous structure or through holes is not essential and only one of the processes may be carried out.

The reason why the process is not essential is that the gas to be sensed may flow in and flow out through a side section of the gas sensing layer 300 even when the process is not carried out on the second electrode 400.

As described above, measurement results of gas sensing characteristics of the manufactured metal oxide semiconductor gas sensor (hereinafter, abbreviated 'gas sensor') having the nanostructure are as follows.

The gas sensing characteristic of the gas sensor provided with the $TiO_2$ gas sensing layer 300 is measured in a tube furnace or a chamber which may heat a substrate. CO and $H_2$ are used as reaction gases and a sample in which a $TiO_2$ thin film is deposited on an IDE (interdigitated electrode) structure was used as a comparative sample.

It is confirmed through FIG. 13 that gas sensitivity of the $TiO_2$ gas sensing layer 300 is increased twice when compared with the comparative thin film sample at 50 ppm of CO, and a reaction rate was 2 seconds, which is at least four times faster than the comparative thin film sample.

In addition, it is confirmed from FIG. 14 that through continuous measurement of $H_2$ gas sensing characteristics of the $TiO_2$ gas sensing layer 300, the gas sensor manufactured through a preferred embodiment of the present invention shows a stable sensitivity change and gas sensitivity is increased 2.5 times when compared with the comparative sample.

Meanwhile, reactivity of the gas sensor provided with the SnO₂ gas sensing layer 300' is measured while alternately flowing 50 ppm of reaction gas CO and dry air in a tube of high temperature.

It is confirmed that through FIG. 15 that gas sensitivity of the SnO₂ gas sensing layer 300' is close to 12 indicating excellent sensitivity at 50 ppm of CO. The reaction rate was within 10 seconds, indicating excellent gas sensor characteristics The present invention has been described above in detail only for the described embodiments, however, various changes and modifications will within the spirit scope of the invention are apparent to those skilled in the art are possible, belonging to the claims that such variations and modifications are attached is granted.

INDUSTRIAL APPLICABILITY

As described above, according to a metal oxide semiconductor gas sensor having a nanostructure and a method for manufacturing the same according to the present invention, since the second electrode 400 is provided in a porous structure so that the gas to be sensed may flow in and flow out, a gas sensing layer 300 of a gas sensor of which electrical conductivity changes when reacting with gas may be formed in a nanostructure by oblique angle deposition, and thus, the gas sensing layer may be easily manufactured, and since the shape of the nanostructure may be also freely formed in a shape to maximize reactivity with the gas, the metal oxide semiconductor having a nanostructure may keep its existing advantage such as maximization of reactivity with a gas while the metal oxide semiconductor may be used as the gas sensing layer 300 interposed between a pair of electrodes.

The invention claimed is:

1. A metal oxide semiconductor gas sensor having a nanostructure, the metal oxide semiconductor gas sensor comprising:
a substrate;
a first electrode formed on the substrate;
a gas sensing layer provided on the first electrode, made of a metal oxide semiconductor which has a nanostructure and of which electrical conductivity changes when the metal oxide semiconductor reacts with gas to be sensed, and formed by oblique angle deposition;
a second electrode formed on the metal oxide semiconductor; and
a control unit for measuring the electrical conductivity of the gas sensing layer to sense the gas by applying a predetermined amount of current through the first and the second electrodes,
wherein the second electrode has a porous structure and the substrate is configured with a certain oblique angle with a flux direction of a deposition material when the second electrode is formed, and wherein
the gas is sensed by easily flowing in and out of the second electrode.

2. The metal oxide semiconductor gas sensor of claim 1, wherein the second electrode has a plurality of crevices in a mesh shape.

3. The metal oxide semiconductor gas sensor of claim 1, wherein the metal oxide semiconductor has the nanostructure of any one shape of a nano-helix, a nano-rod, an inclined nano-rod, a nano-wire, a nano-ribbon, a nano-spring and a nano-cone.

4. The metal oxide semiconductor gas sensor of claim 1, wherein the metal oxide semiconductor is made of at least one of SnO2, TiO2, ZnO, CuO, NiO, CoO, In2O3, WO3, MgO, CaO, La2O3, Nd2O3, Y2O3, CeO2, PbO, ZrO2, Fe2O3, Bi2O3, V2O5, VO2, Nb2O5, Co3O4 and Al2O3.

5. The metal oxide semiconductor gas sensor of claim 1, wherein each the first and second electrodes is made of at least one of Pt, Au, Ti, Pd, Ir, Ag, Ru, Ni, STS, Al, Mo, Cr, Cu, W, ITO (Sn doped In2O3) and FTO (F doped SnO2).

6. The metal oxide semiconductor gas sensor of claim 1, wherein the substrate is provided with an insulating substrate made of an insulation material, or a conductive substrate insulated with an insulation material.

7. The metal oxide semiconductor gas sensor of claim 6, wherein the substrate is provided in any one of an alumina substrate, a sapphire substrate and a silicon substrate, and a metal substrate, a conductive oxide substrate and a conductive polymer substrate on which an insulation layer made of an insulation material is deposited.

8. The metal oxide semiconductor gas sensor of claim 1, wherein the second electrode comprises one or more through holes formed by micro-patterning.

9. The metal oxide semiconductor gas sensor of claim 1, wherein the second electrode is provided with an electrode pad for measuring an electrical property through a probe and for wire-bonding to an external circuit.

10. A method for manufacturing a metal oxide semiconductor gas sensor having a nanostructure, the method comprising:
forming a first electrode on a substrate;
forming a gas sensing layer by depositing a deposition material at a predetermined oblique angle with respect to an upper surface of the first electrode through oblique angle deposition to allow a metal oxide having a nanostructure to be formed on an upper surface of the first electrode;
forming a second electrode on the gas sensing layer; and
connecting a control unit measuring electrical conductivity of the gas sensing layer to the first and second electrodes,
wherein the forming of the second electrode comprises deposition of the substrate with a certain oblique angle with a flux direction of a deposition material wherein the second electrode is formed having a porous structure on the gas sensing layer by using the oblique angle deposition, and wherein
gas is sensed by easily flowing in and out of the second electrode.

11. The method of claim 10, wherein the forming of the second electrode comprises forming the second electrode having a plurality of crevices in a mesh shape on the gas sensing layer by using the oblique angle deposition.

12. The method of claim 10, wherein the forming of the gas sensing layer is forming the gas sensing layer by depositing the metal oxide while rotating the first electrode at a predetermined speed in a predetermined direction in a state where a flux line of the metal oxide as a deposition material makes a predetermined oblique angle with the upper surface of the first electrode.

13. The method of claim 10, wherein the forming of the gas sensing layer is forming the gas sensing layer by depositing the metal oxide in a state where a flux line of the metal oxide as a deposition material makes an angle in the range of 30 to 90 degrees, exclusive of 90, with a vertical line to the upper surface of the first electrode.

14. The method of claim 10, further comprising forming a plurality of through holes by micro-patterning the second electrode to allowing the gas to easily flow into and out of the gas sensing layer.

15. The method of claim 10, further comprising heat-treating the gas sensing layer at 300° C. to 1,000° C. so that the gas sensing layer is crystallized.

16. The method of any claim 10, further comprising performing heat treatment at 200° C. to 1,000° C. so that the gas sensing layer makes ohmic contact to the first and second electrodes.

* * * * *